(12) United States Patent
Zaluzec

(10) Patent No.: US 6,548,810 B2
(45) Date of Patent: Apr. 15, 2003

(54) SCANNING CONFOCAL ELECTRON MICROSCOPE

(75) Inventor: Nestor J. Zaluzec, Bolingbrook, IL (US)

(73) Assignee: The University of Chicago, Chicago, IL (US)

(*) Notice: Subject to any disclaimer, the term of this patent is extended or adjusted under 35 U.S.C. 154(b) by 91 days.

(21) Appl. No.: 09/920,492

(22) Filed: Aug. 1, 2001

(65) Prior Publication Data

US 2003/0025075 A1 Feb. 6, 2003

(51) Int. Cl.$^7$ ............................................. G01N 23/00

(52) U.S. Cl. ......................... 250/306; 250/310; 250/311

(58) Field of Search .............................. 250/306, 311, 250/310

(56) References Cited

U.S. PATENT DOCUMENTS

| | | | |
|---|---|---|---|
| 3,013,467 A | | 12/1961 | Minsky |
| 4,812,652 A | * | 3/1989 | Egle et al. ................. 250/311 |
| RE33,275 E | * | 7/1990 | Wardell et al. ............ 250/305 |
| 5,493,116 A | * | 2/1996 | Toro-Lia et al. ........... 250/310 |
| 5,510,624 A | | 4/1996 | Zaluzec |
| 6,448,556 B1 | * | 9/2002 | Cowley et al. ............. 250/311 |

OTHER PUBLICATIONS

M. Minsky, "Memoir on Inventing the Confocal Scanning Microscope", Scanning, vol. 10, 128–138 (1988).

X. Su et al., "Quantitative nanoscale metrology study of Cu/SiO$_2$ Interconnect technology using transmission x-ray microscopy", Applied Physics Letters, vol. 77, No. 21, Nov. 20, 2000, pp. 3485–3487.

The Handbook of Biological Confocal Microscopy, by James Pawley, Editor, IMR Press, 1989, pp. 1–13.

* cited by examiner

Primary Examiner—John R. Lee
Assistant Examiner—Phillip A Johnston
(74) Attorney, Agent, or Firm—Joan Pennington

(57) ABSTRACT

A scanning confocal microscope and methods are provided for configuring scanning confocal microscopes for imaging specimens, such as, high resolution imaging of thick non-optically transparent specimens including imaging of buried or subsurface features of thick non-optically transparent structures. The scanning confocal microscope, such as a scanning confocal electron microscope (SCEM), is configured to image structures buried in thick specimens, such as specimens greater than eight microns thick, utilizing confocal imaging principles. A scanning confocal microscope includes an illumination source, a specimen, and a detector. The illumination source provides a focused radiation beam that is applied to the specimen. The detector detects an interaction signal from the specimen. The scanning confocal microscope is configured to operate in the confocal imaging mode, where the imaging source, specimen and detector are arranged to be located at conjugate image points. The focused radiation beam provided by the illumination source includes an electron beam, a proton beam, an ion beam, or an x-ray beam. The focused radiation beam provided by the illumination source is capable of penetrating thick non-optically transparent specimens, unlike visible light or optical probes that cannot penetrate significant depths in optically dense specimens. The incident probe is sequentially scanned across a region of interest of the specimen and the net integrated confocal intensity at each point is detected and used to provide an image display. A scanning confocal electron microscope (SCEM) is provided that permits resolutions better than 100 nanometers for materials as thick as 8–10 microns. The image resolution provided is equal to or better than typical high flux x-ray sources, while operating at speeds up to one hundred times faster and the scanning confocal microscope can be located in a conventional laboratory space.

24 Claims, 14 Drawing Sheets

CONFOCAL IMAGING MODE

PRIOR ART TEM
IMAGING MODE

PRIOR ART STEM
IMAGING MODE

CONFOCAL
IMAGING MODE

CONVENTIONAL TEM
IMAGE OF ~4 μm
THICK SEMICONDUCTOR
DEVICE

SCEM IMAGE OF ~4 μm
THICK SEMICONDUCTOR
DEVICE 200

TOP SURFACE
SCEM IMAGE 1100

BOTTOM SURFACE
SCEM IMAGE 1102

SCANNING CONFOCAL ELECTRON MICROSCOPE

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates generally to scanning, transmission, and scanning transmission electron microscopes, confocal and scanning confocal (optical) microscopes as well as to x-ray microscopy instrumentation capable of producing images of objects at varying resolutions ranging from the macroscopic to nanometer regime. More particularly, the present invention relates to an electron optical device or a scanning confocal microscope and methods for imaging specimens, such as, high resolution imaging of thick non-optically transparent specimens including imaging of structures buried in thick non-optically transparent specimens.

DESCRIPTION OF THE RELATED ART

A wide range of instruments, such as scanning, transmission, and scanning transmission electron microscopes, confocal and scanning confocal optical microscopes as well as to x-ray microscopy instrumentation, can be used today for microscopic studies of materials. Generally confocal and scanning confocal optical microscopy (COM/SCOM) employ visible light as their illumination source to produce a representative image of the specimen, while the electron and x-ray microscopes correspondingly utilize electrons and x-rays as sources. Each of scanning, transmission, and scanning transmission electron microscopes, confocal and scanning confocal optical microscopes as well as to x-ray microscopy instrumentation is capable of producing images of objects at varying resolutions ranging from the macroscopic (mm) through micrometer ($\mu$m) to nanometer (nm) regime.

Confocal optical microscopy (COM), due to its dependence upon visible light is limited to applications where researchers study only the surface of optically dense objects, or the internal structure of optically transparent objects which permit light to be reflect or be transmitted from and/or through subsurface features. In Scanning Confocal Optical Microscope (SCOM), images are obtained using a confocal technique, where the imaging source, sample and detector all lie in conjugate planes, thus reducing the extraneous light scattering from blurring the image. However, the use of light precludes the use of non-transparent specimens that make up the most of the physical science specimens. The COM and Scanning Confocal Optical Microscope (SCOM) typically operates at resolutions of ~500 nm. Of these two modes, the latter transparent mode is the most prolific application particularly in the area of life sciences where the SCOM has made a major impact upon that community.

The scanning electron microscope (SEM) has also gained widespread acceptance as a high resolution (~10 nm) device for studies of the surfaces of materials of all descriptions in both the life and physical science area, owing to the fact that its imaging signal is principally generated and localized to the near surface zone. The transmission and scanning transmission electron microscope (TEM/STEM) is most often the instrument of choice for studying the internal structure of materials at moderate to very high resolution (~0.1 nm); however, with the caveat that the specimen of interest must be rendered extremely thin or <100 nm. Finally, the modern x-ray and scanning transmission x-ray microscope (XTM/STXM) utilizes a focused x-ray beam to penetrate thick sections of materials >5 $\mu$m to study, in projection, a materials' internal structure. Generally these x-ray instruments are located at synchrotron radiation sources and used for studying the internal structure of relatively thick materials, which are not amenable to study by any of the former devices. Currently these x-ray microscopes operate at moderate resolutions of ~200 nm. The cost of synchrotron radiation sources, such as the national synchrotron-radiation light source at Argonne National Laboratory, are generally in the range of hundreds of millions of dollars.

In today's technologically driven society, a greater and greater number of important devices are being constructed on an ever decreasing size scale. At the same time they are also being fabricated as multi-layered structures to maximize density and minimize size. The most well known example of this construct is the semiconductor microprocessor that can have from one to more than 5 layers within a total thickness on the order of 5–10 microns. Within the individual layers important features can vary in size from 100 $\mu$m to the 10 nm level. The role of microscopy when applied to these devices is to characterize the structure of such objects, particularly in scenario where there is some material failure particularly in the sub-micrometer to nanometer scale.

In order to study the detailed internal structure of buried features in optically dense materials from either a fundamental or failure analysis standpoint, researchers today must painstakingly prepare cross-sectional, or plan-view samples of appropriate thickness for use in either the TEM/STEM or the XTM/STXM, since neither the COM/SCOM nor the SEM allow the inspection of internal (buried) layers and/or components. While both TEM/STEM and XTM/STXM allow a modicum of observation to be facilitated, both these generic types of instruments have their respective limitations. While the resolution of the TEM/STEM is orders of magnitude better than the XTM/STXM, this is only true for extremely thin samples. In the TEM/STEM images are mainly produced by measuring the elastically scattered electrons transmitted through the sample, and hence are ultimately limited by this process. To utilize the TEM/STEM researchers must prepare thin sections (<100 nm thick) of a material, and as a result sacrificing adjacent structures in the process. Sample preparation is thus a destructive procedure in the TEM/STEM instrumentation and limits the type of observations that can be conducted. In contrast, the XTM/STXM, is less affected by the scattering process of the primary illumination source, utilizes elastic and inelastic scattering to produce image, and typically employs sample that are tens of micrometers thick. XTM/STXM, however, suffers from reduced resolution when compared to thin film TEM work, long acquisition times, limited fields of view and more importantly, operationally complex procedures which are slow and resource consuming, requiring expensive and frequently large physical facilities such as synchrotron based x-ray sources.

A principal object of the present invention is to provide a scanning confocal microscope and methods for imaging specimens, such as, high resolution imaging of thick non-transparent specimens including imaging of structures buried in thick non-transparent specimens.

Another object of the present invention is to provide an improved method for implementing the imaging of buried or subsurface features of the structure of technologically complex objects such as semiconductor devices at high resolution.

Another object of the present invention is to provide improved methods for implementing a scanning confocal electron microscope (SCEM).

Another object of the present invention is to provide a scanning confocal microscope and methods for imaging specimens, such as, high resolution imaging of thick non-transparent specimens including imaging of structures buried in thick non-transparent specimens substantially without negative effect and that overcome some disadvantages of prior art arrangements.

SUMMARY OF THE INVENTION

In brief, a scanning confocal microscope and methods are provided for configuring scanning confocal microscopes for imaging specimens, such as, high resolution imaging of thick nontransparent specimens including imaging of buried or subsurface features of thick nontransparent structures. Novel methods are provided for configuring a scanning confocal microscope, such as a scanning confocal electron microscope (SCEM), to image structures buried in thick specimens, such as specimens greater than five microns (micrometers) thick, utilizing confocal imaging principles.

A scanning confocal microscope includes an illumination source, a specimen, and a detector. The illumination source provides a focused radiation beam that is applied to the specimen. The detector detects an interaction signal from the specimen. The scanning confocal microscope is configured to operate in the confocal imaging mode, where the imaging source, specimen and detector are arranged to be located at conjugate image points by means of lenses while scanning is accomplished by means of an illumination deflection system.

In accordance with features of the invention, the focused radiation beam provided by the illumination source includes an electron beam, a proton beam, an ion beam, or an x-ray beam. The focused radiation beam provided by the illumination source is capable of penetrating thick non-optically transparent specimens, unlike visible light or optical probes that cannot penetrate significant depths in optically dense specimens. The incident probe is sequentially scanned across the region of interest of the specimen and the net integrated confocal intensity at each point is detected and used to provide an image display.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1A:
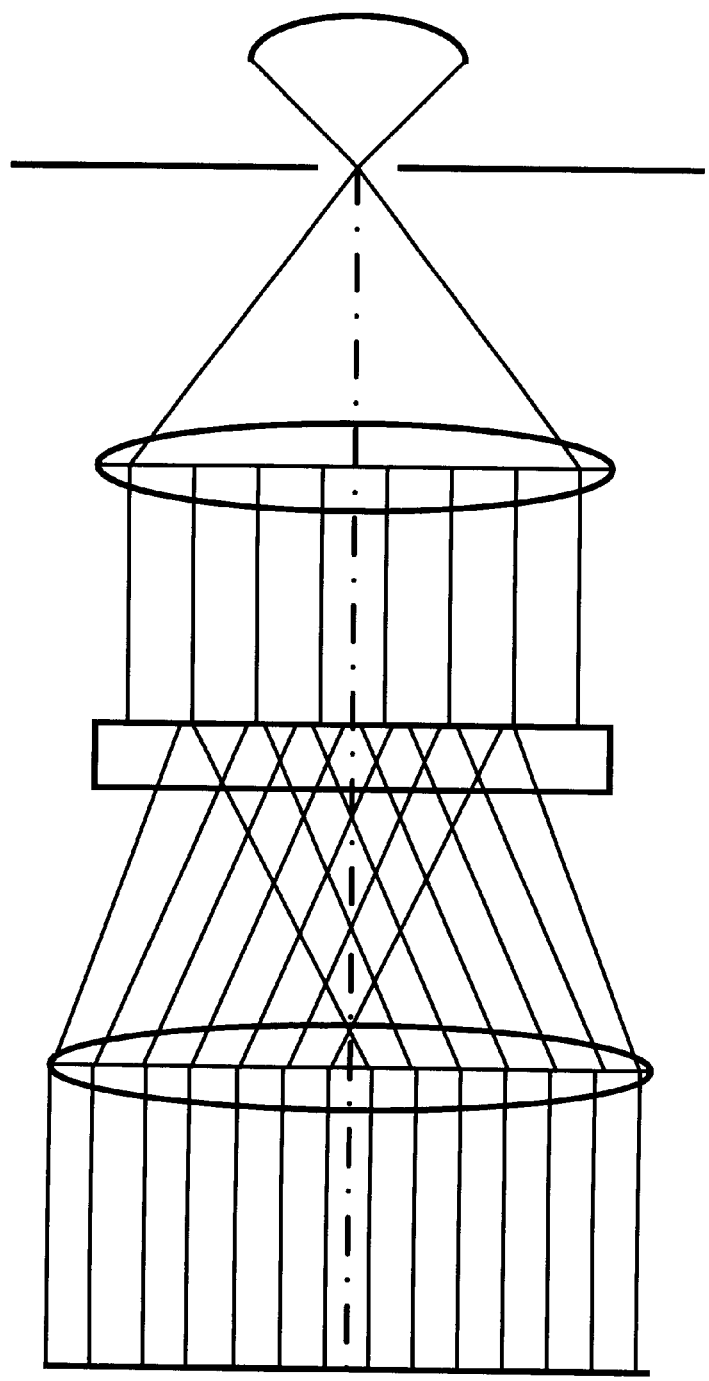
FIG. 1A illustrates an Electron-Optical configuration of an electron microscope in a conventional TEM imaging mode.

In accordance with features of the invention, a scanning confocal microscope, such as, a scanning confocal electron microscope (SCEM), is provided which permits high image resolution, for example, better than 100 nanometers for materials as thick as 8–10 microns. The resolution enabled by the invention is currently equal to or better than typical high flux x-ray sources, while operating at speeds up to one hundred times faster, and that can be located in a conventional laboratory space. A method of the invention by which an Electron Optical Column (EOC) is uniquely configured to allow the imaging of thick specimens, for example, 8–10 micrometers. In this configuration, the EOC operates as a Scanning Confocal Electron Microscope (SCEM).

In accordance with features of the invention, the SCEM is an electron-optical application of the confocal imaging principle. SCEM merges the concepts of confocal imaging with the ease of use of an SEM, the resolution of the TEM and the depth penetration of the STXM. Using this invention, a single individual can operate a complete instrument which is small enough be housed within a standard 25×25 ft laboratory space. Using the SCEM an operator can image and analyze semiconductor specimens up to 8–10 microns thick at resolutions nearly two times better than the current generation XTM/STXM. This invention also operates at acquisition times which can be up to one hundred times faster, and built and operated at a cost which can be more than one hundred times lower than an x-ray microscope and associated synchrotron facility. In addition, the field of view of this invention allows large area, such as 1 mm×1 mm areas to be imaged in less than one minute, and enables real time navigation and adjustment by the operator to simply zoom to any area of the sample, for closer inspection or analysis.

In accordance with features of the invention, the addition of simple ancillary detectors, such as secondary electron, backscattered and x-ray energy dispersive spectrometers also permit routine surface imaging and elemental analysis to be conducted at the same time. This is a sufficiently small footprint and operating cost that such an instrument can even be collocated, for example, at semiconductor fabrication or analysis facilities without difficulty.

An embodiment of the present invention has been implemented and reduced to practice that provides resolutions of less than 100 nm in semiconductor samples of 8 micron thickness and that under appropriate conditions has demonstrated spatial resolutions better than 20 nm. This embodiment of the present invention is based upon an electron-optical column employing a 100–300 kV field emission gun, a series of pre and post lenses, probe deflection systems, signal detectors, vacuum systems, and a specimen stage.

It should be understood that the invention is not limited to the use of an electron probe as the illumination source, the invention is equally applicable to any device which can employ a pre specimen focused illumination and post specimen focused illumination and projection lenses and whose resolution and signal is limited by either multiple inelastic and/or high angle scattering. It should be understood that while the scanning confocal microscope of the present invention is generally illustrated and described as a scanning confocal electron microscope (SCEM), the scanning confocal microscope of the present invention also includes a scanning confocal proton microscope (SCPM), a scanning confocal ion microscope (SCIM), and a scanning confocal x-ray microscope (SCXM). As such it should be understood that principles of the invention are applicable to any microscope employing alternative focused probes, for example, protons, ions, and/or x-rays. While a principle application of the scanning confocal microscope of the present invention is imaging of semiconductor devices, it should be understood that the present invention is not limited to this application and is equally useful for imaging various other materials.

Scanning confocal electron microscope (SCEM) of the invention enables imaging of specimens of 8–10 microns thickness. In the known art there are, as described previously, only two types of instruments that are applicable to imaging structures in this thickness regime, the TEM/STEM and the XTM/STXM. These devices employ respectively either high energy electrons (100–1000 keV) and/or low to medium energy x-rays. Either instrument by their nature have sufficient energy to penetrate great depths within a solid. X-ray microscopes derive their imaging capabilities by exploiting this fact, but are unwieldy devices and generally are not amenable to high throughput scenarios, where large numbers of samples are studied in short time scales. Commercially available transmission electron microscopes in this operating regime (100–1000 KeV) typically have optics and operating modes designed primarily to form images with elastically scattered electrons through small angles. This elastic signal rapidly diminishes with sample thickness and is nearly non-existent after ~1–2 $\mu$m in thickness. Known transmission electron microscopes have not been designed to optimally recover the signal from extremely thick regions of a sample.

Figure 1B:
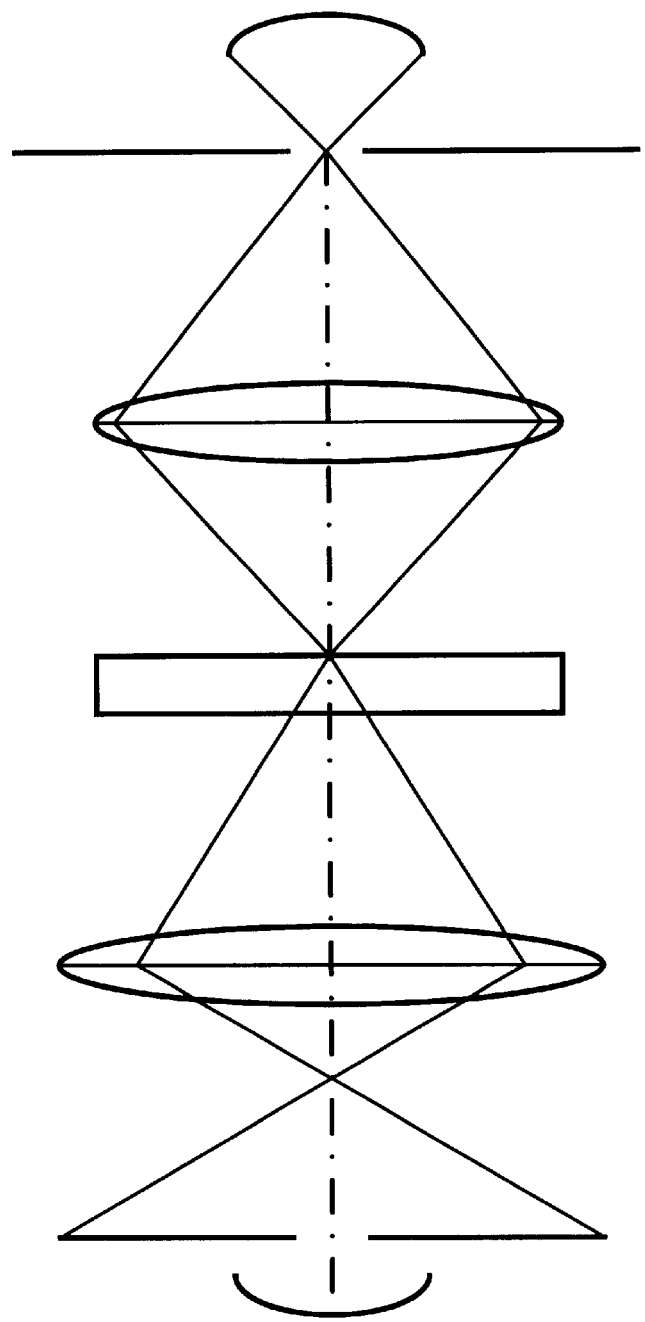
FIG. 1B illustrates an Electron-Optical configuration of an electron microscope in a conventional STEM imaging mode.
Figure 1C:
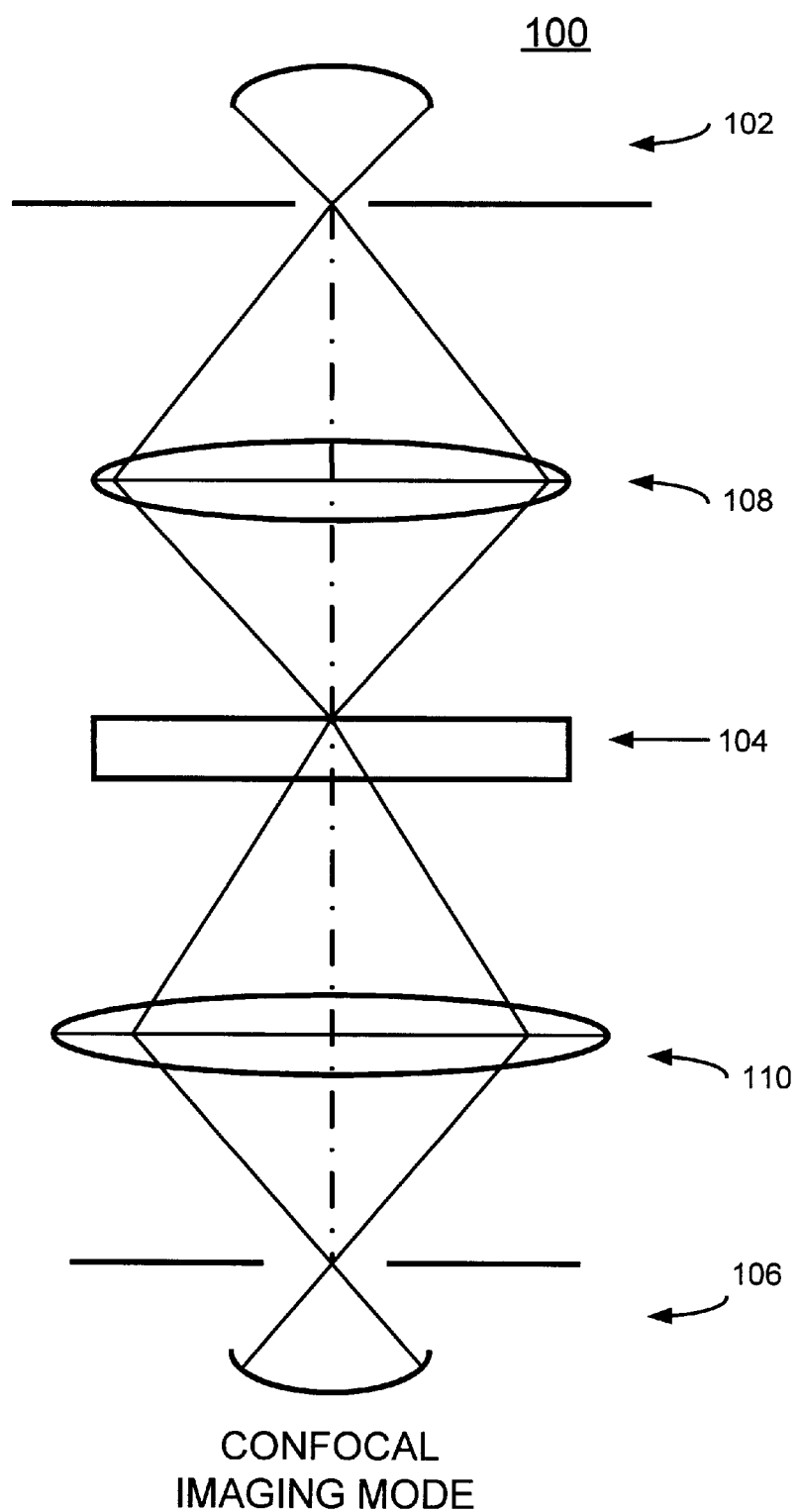
FIG. 1C illustrates an Electron-Optical configuration of an electron microscope in a confocal imaging mode or SCEM of the preferred embodiment.

Referring now to FIGS. 1A, 1B and 1C, there are shown three different operating configurations of an electron microscope. In FIG. 1C, in accordance with features of the invention an electron microscope generally designated by the reference character 100 is configured to operate in a confocal imaging mode. Electron microscope or detector system 100 overcomes the limitations of the cumbersome nature of the XTM/STXM as well as the thickness limitations of the TEM/STEM. Electron microscope 100 includes an illumination source 102, a sample or specimen 104 and a detector 106 each adjusted so that all are located at conjugate image points. An electron optical system, such as a single pre-specimen lens or multiple pre-specimen lens system 108 takes the electron source to a focused radiation beam to an illumination point on the specimen 104. Then a single post-specimen lens or multiple post-specimen lens system 110 is utilized to focus from this specimen illumination point onto detector 106. In the confocal imaging mode illustrated in FIG. 1C, the electron microscope 100 sequentially illuminates points of a sample 104 that are confocal to an aperture. Then scanning sequential illuminated points of the sample 104 forms a sample image. This is contrary to the conventional operating configurations of an electron microscope which is operated in the TEM mode as illustrated in FIG. 1A or the STEM mode as illustrated in FIG. 1B, where the instruments are configured in a mode having two-dimensional conjugate image planes. In TEM or STEM the available imaging planes are generally termed Focussed Image Plane and the Back Focal Plane.

In the SCEM mode of FIG. 1C, the pre-specimen lens or lens system 108 is adjusted to a focused probe configuration, while the post-specimen lens or lens system 110 is configured to bring the post-specimen scattering distribution to a conjugate image point. This results in maximizing the angular range of both elastic and inelastic scattered electrons measured by detector 106 which is conjugate to the imaging probe and the specimen illumination zone. While the term conjugate image point is used above, it is understood that this "point: has finite dimensions. These dimensions are defined by the post specimen lens settings and the size of the detector and any apertures employed. The key difference between SCEM and TEM or STEM being that the integrated intensity of the total scattered information within the entire detection zone (conjugate image point) is used to form a single measure of the scattering intensity from a point on the specimen, rather than the intensity within an image plane in TEM or STEM. In SCEM, the incident probe is sequentially scanned across the region of interest of the specimen 104 and the net integrated confocal intensity at each point is detected and then used to modulate an image display, akin to operation of an SEM or STEM. Not shown in FIGS. 1A and 1B, is that in known commercial TEM/STEM instruments the post specimen lenses are adjusted to pass primarily the elastically scattered electrons from the sample, the inelastic scattering thus contributing to a diffuse background that blurs the image. In contrast in the SCEM the inelastically scattered intensity is constructively used to enhance the image intensity.

Figure 2A:
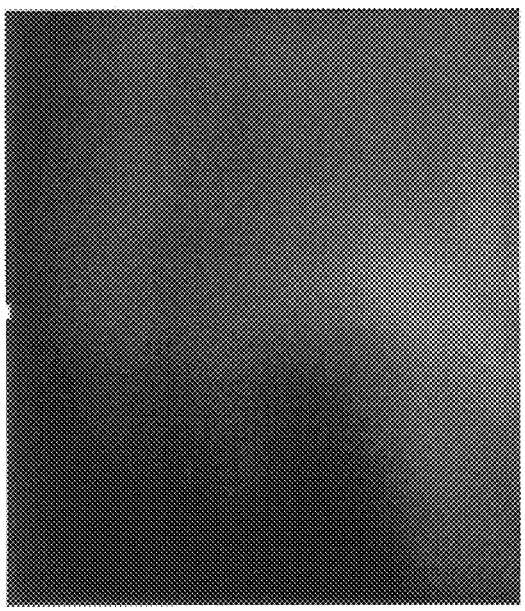
FIGS. 2A and 2B respectively illustrates image resolution in a TEM image of the conventional TEM imaging mode of FIG. 1A as compared to SCEM image of the confocal imaging mode or SCEM of FIG. 1C of the preferred embodiment where both images are of the the same object with the same magnification.
Figure 2B:
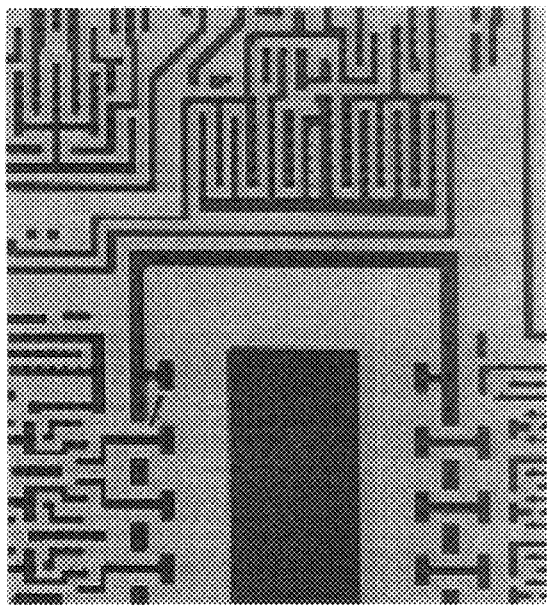

FIGS. 2A and 2B respectively illustrate image resolution in a TEM image of the conventional TEM imaging mode of FIG. 1A as compared to a SCEM image of the confocal imaging mode or SCEM 100 of FIG. 1C of the preferred embodiment. The magnitude of image blurring is shown in the TEM image of FIG. 2A which corresponds to a nominally ~4 $\mu$m thick semiconductor sample, where the image is blurred beyond recognition. In comparison, using the same sample but operating in SCEM mode, the contribution of inelastic signal to the image is constructively utilized and the image resolution is dramatically improved as seen in FIG. 2B. In normal transmission mode, post specimen lenses of an electron microscope, if available, are configured to collect and reconstruct the specimen image from those electrons that are elastically scattered through thin specimens. If a thick specimen is viewed under normal mode virtually no usable image is generated due to the very small numbers of elastically scattered electrons and the concomitant pronounced blurring from the inelastically scattered electrons as seen in FIG. 2A. In confocal mode of the preferred embodiment, the collection and image reconstruction from electrons that have been scattered by all processes from the thick specimen provide an excellent image of structures buried within the thick specimen as seen in FIG. 2B. Ultimate image resolution in the SCEM mode is controlled by a combination of the incident probe size, probe current, accelerating voltage, and the depth in the sample of the feature to be imaged.

Figure 3:
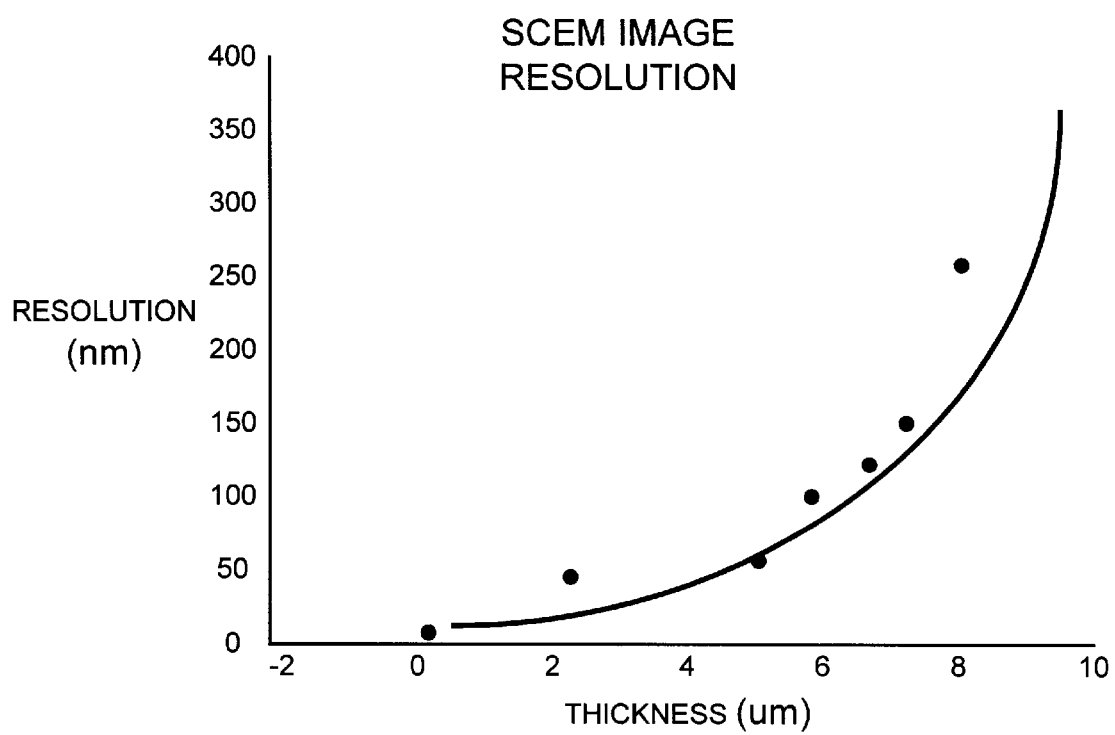
FIG. 3 is a chart illustrating experimental measurements of SCEM image resolution shown relative to the vertical axis as a function of specimen thickness shown relative to the horizontal axis in accordance with the preferred embodiment.

FIG. 3 illustrates experimental measurements of SCEM image resolution as a function of specimen thickness in accordance with the preferred embodiment. In FIG. 3, the illustrated SCEM image resolution represents experimental measurements with the confocal imaging mode of SCEM 100 of FIG. 1C of the preferred embodiment.

Figure 4:
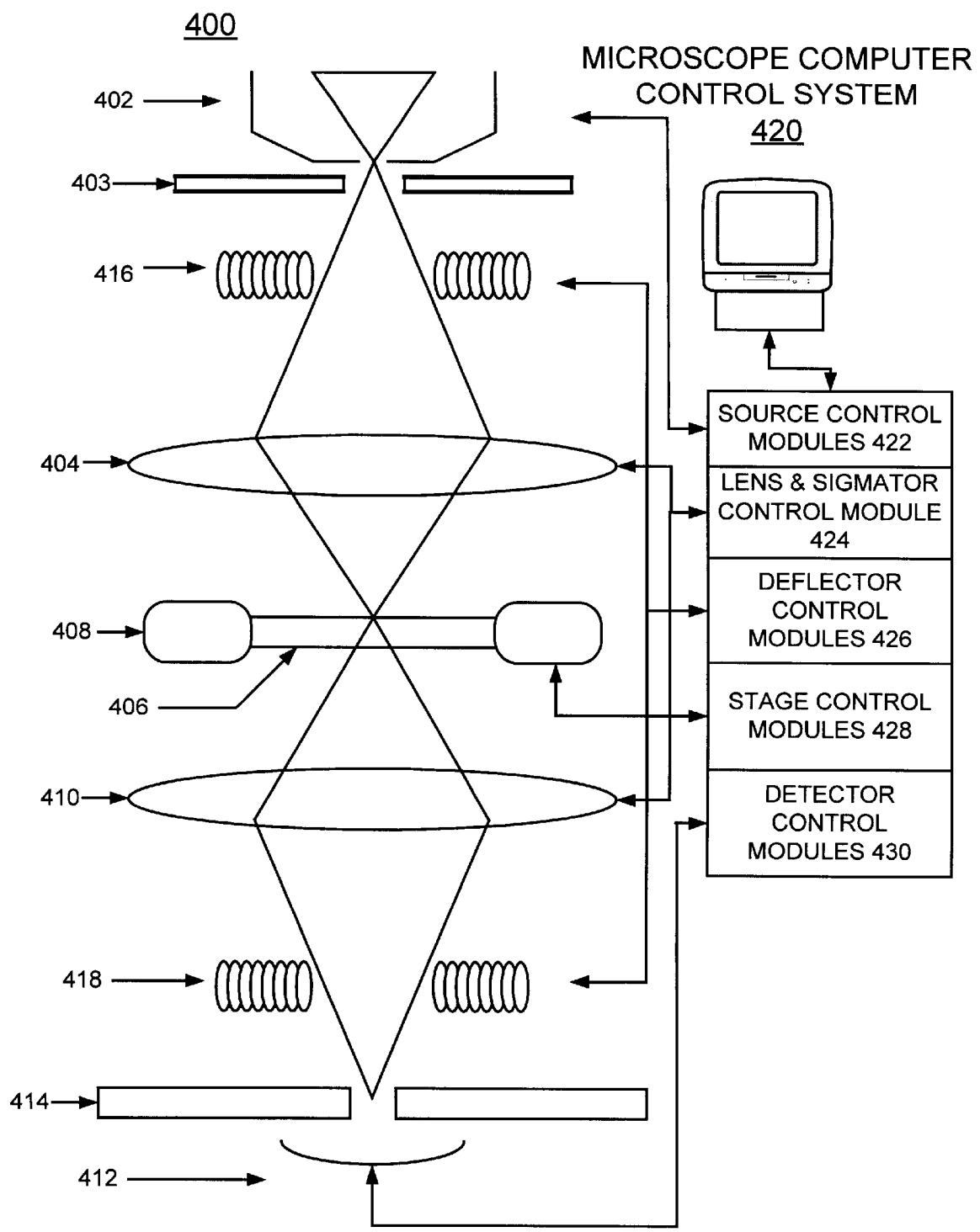
FIG. 4 illustrates, in more detail than FIG. 1C, a basic SCEM configuration in accordance with the preferred embodiment.

Referring now to FIG. 4, there is shown a more detailed SCEM configuration generally designated by the reference character 400 in accordance with the preferred embodiment. In accordance with methods of the invention, near real time observation and characterization of sub-surface or buried features is enabled in thick, such as ~8–10 microns, optically dense materials at high spatial resolution. This technique relies upon subjecting an optically dense specimen to penetrating radiation in the form of a focused beam from an aperture limited illumination source 402 including an illumination aperture 403. At least a single lens system 404 directs the focused beam onto an optically dense specimen 406. Specimen 406 is held by a specimen translation stage 408. The fullest possible measure of scattered intensity distribution of any resulting interaction product signal, both primary and secondary, is simultaneously focused with at least one post specimen lens 410 to at least a single conjugate point detector 412 beyond a field limiting aperture 414. A pre-specimen double deflection system 416 preferably is used to translate the penetrating radiation to the specimen 406. To insure that the interaction product signal is measured to the maximum extent by the post-specimen detector 412, a suitably arranged de-scanning system 418 is located on the exit side of the specimen and is used to direct the post specimen focused signal through aperture 414 to the detector 412. The location of the pre-specimen and post specimen deflection systems 416 and 418 may be before, after or in the case of multiple lenses in between the lens 404 and 410.

SCEM 400 includes a microscope computer control system generally designated by the reference character 420 in accordance with the preferred embodiment. Microscope computer control system 420 is used for operation of the SCEM 400 and also can be used for display the experimental results. Microscope computer control system 420 includes multiple microscope analog subsystem control modules arranged for operatively controlling components of SCEM 400, as shown. The microscope analog subsystem control modules include source control modules 422, lens and sigmator control modules 424, deflector control modules 426, stage control modules 428, and detector control modules 430. Microscope computer control system 420 is illustrated in simplified form sufficient for an understanding of the present invention because the utility of the present invention is not limited to details of such microscope computer control system.

In order to insure the maximum versatility of the instrument the specimen translation stage 408 is capable of 6 axis motion (three axes of translation X,Y,Z, two axes of tilt X, Y, and one of rotation Z), including the ability to completely flip the specimen 406 over exchanging the illumination (or top) and transmission (or bottom) surfaces. The specimen translation stage 408 can be implemented, for example, with a 6 axis goniometer.

Optionally, additional detectors may be located such as secondary, backscattered electron and x-ray energy dispersive detectors either above or below the specimen 406 to measure ancillary signals. These could, for example, be located intermediate between the lens 404 and the specimen 406 or between the specimen 406 and lens 410.

The specimen 406 and stage 408 are interfaced to SCEM 400 by means of an airlock to permit the rapid and efficient exchange of specimens as would be required for during failure analysis. The instrument may also be equipped with a plasma cleaning system to enable cleaning of the sample, stage, and the internal components of the SCEM 400 to prevent contamination of the field of view. U.S. Pat. No. 5,510,624 issued to Nestor J. Zaluzec on Apr. 23, 1996, entitled Simultaneous Specimen and Stage Cleaning Device for Analytical Electron Microscope, and assigned to the present assignee discloses such an airlock and plasma cleaning system. The subject matter of the above-identified patent is incorporated herein by reference.

The illumination source 402 providing principle penetrating radiation for the SCEM 400 is a high-energy, high-brightness, electron beam illumination source operated in the range of 100–1000 kV, the typical operating values being 300–400 kV for application to the observations of a nominal 8 micron thick semiconductor sample. SCEM 400 preferably employs a field emission electron source, however, instruments of lesser capability can be constructed using alternative electron sources such as Lanthamium Hexabordie (LaB6), or Tungsten (W) systems. These lesser systems generally will require additional pre-specimen lenses 404 to achieve comparable performance. In addition to the electron source, the illumination source 402 may include associated lenses, apertures and related peripherals needed to create a well-formed electron beam.

The function of the pre-specimen scanning system 416 is to facilitate rapid illumination of the specimen in a point by point mode, keeping the illumination source nearly perpendicular to the XY plane of the instrument, while the function of the post specimen de-scanning system is to compensate for any motion of the post-specimen scattering distribution caused by scanning the illumination and returning this distribution to the conjugate imaging detector. This is particularly important during large field of view conditions, where the incident illumination may be used to scan over regions of interest in the millimeter regime. The general methodology of the scanning and obtaining magnification employed in the SCEM is identical to that which used in a conventional SEM and is known in the art.

Figure 5:
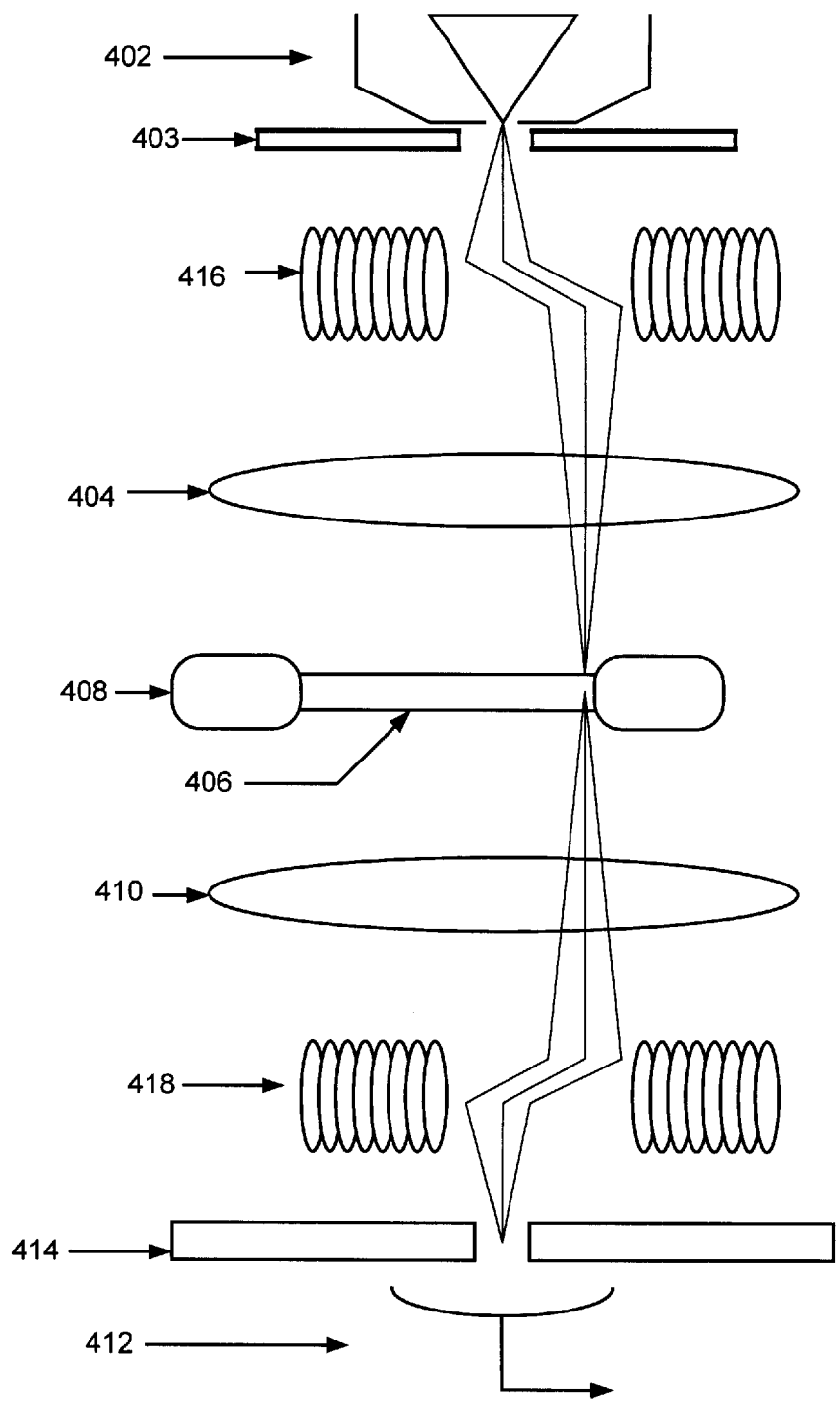
FIG. 5 illustrates de-scanning applied to the SCEM operating mode in accordance with the preferred embodiment.

Having reference to FIG. 5 in accordance with another feature of the invention, synchronous de-scanning is used to return the scattered distribution to the point detector for SCEM imaging of the preferred embodiment. FIG. 5 illustrates this synchronous de-scanning in a double deflection SCEM configuration generally designated by the reference numeral 500. In FIGS. 5, 6A, 6B, and 7–9, the same reference numbers as used in FIG. 4 are used for identical or similar components.

It should be understood that judiciously configured lenses and single deflection scan coils or deflectors can be arranged to accomplish this same task of double deflection SCEM configuration 500 if multiple lenses are employed and the deflectors are located appropriately. This may include repositioning of the respective lenses and deflection coils with respect to each other and the specimen. Should the SCEM field of view be limited to a smaller XY spatial extent, such as microns instead of millimeters, then it is possible to eliminate the de-scanning system from an implementation of this invention, for example, by substituting a different detector 412 and aperture 414, while a loss of performance at low magnification results.

In general, the detector system 412 in the SCEM 400 is a signal measuring device and typically for the case of electrons can be implemented, for example, with a scintillator and photomultiplier combination. Using electronic amplification the intensity output of this detector 412 is measured, stored and processed to produce an image which is displayed on a suitable monitor. Structural features in the sample are made visible by exploiting the fact that there is always a fraction of the transmitted scattering distribution which is lost (by various scattering and/or absorption mechanisms) as the illumination source propagates through the specimen. This lost signal varies with composition and structure, and although it may be only be a small fraction, the difference between adjacent areas can be amplified, integrated and used to produce an image.

In accordance with features of the invention, further image contrast can be introduced into the SCEM image by four additional methods as illustrated and described with respect to FIGS. 6A, 6B, 7, 8 and 9, each of which may be applied individually or in various combinations.

Figure 6A:
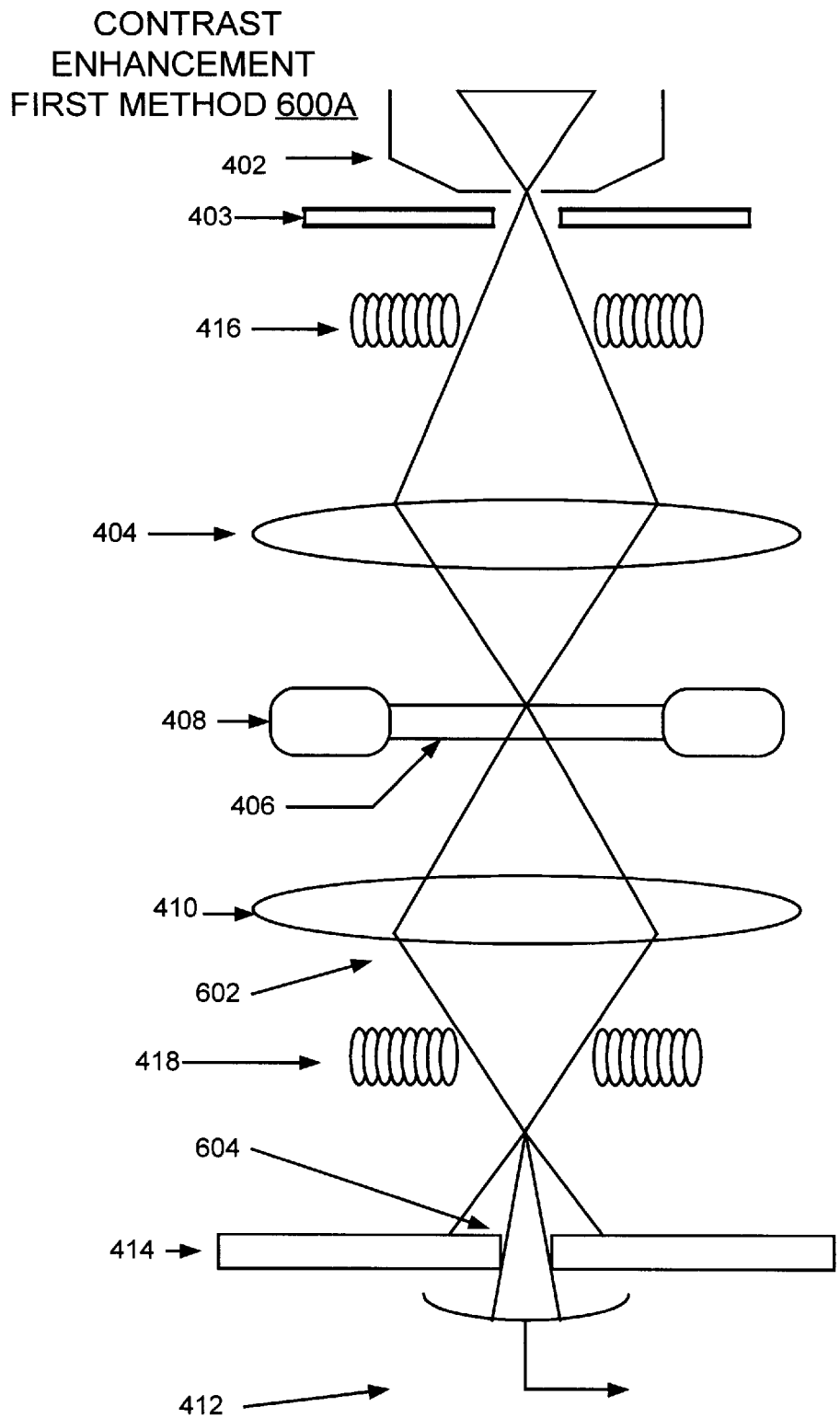
FIGS. 6A and 6B illustrate a respective first contrast enhancement method of adjusting post specimen lens focus to exclude some high angle scattering or for limited selection of the depth of focus in accordance with the preferred embodiment.
Figure 6B:
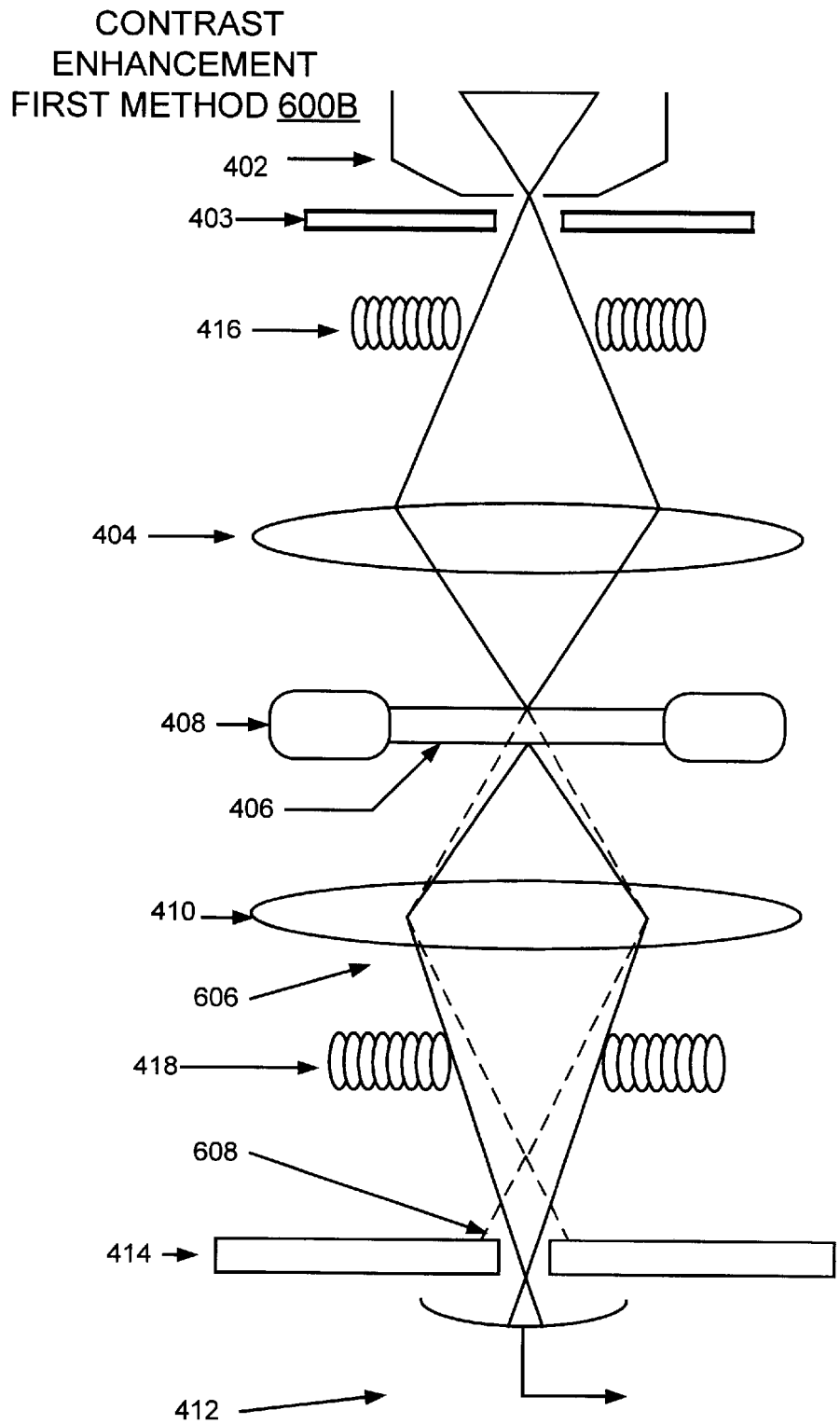

Referring now to FIGS. 6A and 6B, a respective SCEM configuration generally designated by the reference numeral 600A, 600B is shown for a first method for implementing further contrast in the SCEM image by adjusting post specimen lens focus to exclude some high angle scattering as illustrated in FIG. 6A or for selection of depth of focus as illustrated in FIG. 6B. In the SCEM configuration 600A for the first method, the post specimen lens system 410 is taken slightly out of the perfect conjugate confocal condition indicated by 602. In this configuration 600A of FIG. 6A, a small amount of the high angle scattered signal indicated by 604 is be allowed to miss the detector 412 by virtue of the field limiting aperture 414. Since the magnitude of the high angle scattered intensity is directly related to the changes in the object density this will increase the available contrast between adjacent areas albeit at a loss of signal. In this SCEM configuration 600 the loss of signal can be compensated for by an increase in the pixel integration time. As illustrated in configuration 600B of FIG. 6B, the post specimen lens system 410 is taken slightly out of the perfect conjugate confocal condition indicated by 606. This method can, in addition, be used as shown in FIG. 6B to permit limited selection of the depth of focus indicated by 608 of the post specimen system 410 allowing the user to selectively image different depths within the sample. This depth of focus ability will be limited by the range of collection angles enabled by the post specimen lens 410 and detector 412.

Figure 7:
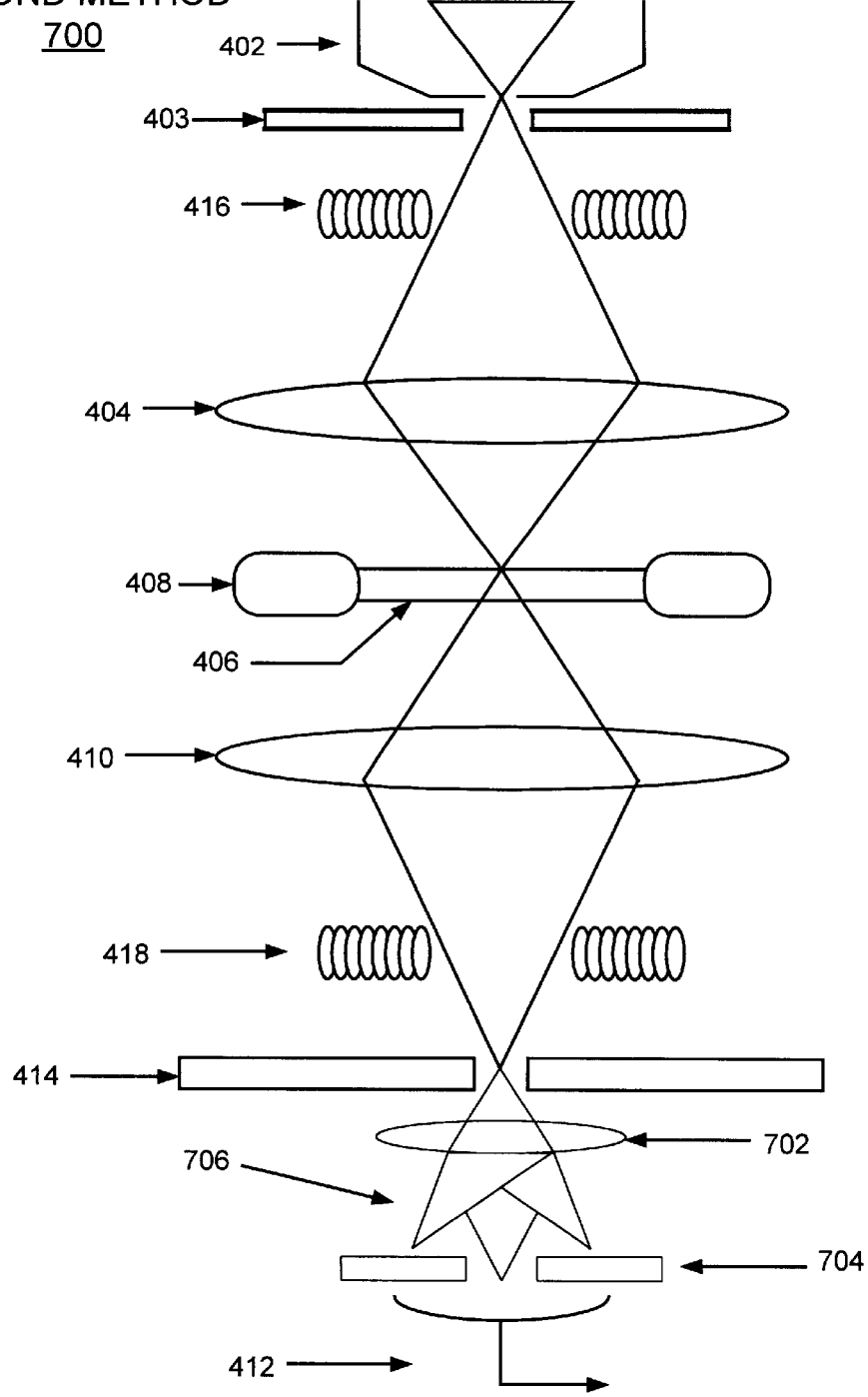
FIG. 7 illustrates a second contrast enhancement method employing inelastic energy band pass filter in accordance with the preferred embodiment.

Referring now to FIG. 7, a SCEM configuration generally designated by the reference numeral 700 is shown for a second method for implementing further contrast in the SCEM image by employing inelastic energy bandpass filtering. A second post-specimen lens or low resolution electron energy analyzer 702 (also called a band pass filter) is provided. The low resolution electron energy analyzer 702 produces a dispersed signal of the inelastically scattered electrons. A portion of inelastic intensity is directed through an energy defining aperture/slit 704 onto detector 412. The multiple beams 706 after the low resolution electron energy analyzer 702 represent different inelastic signals which in FIG. 7 are dispersed horizontally. By adjusting the band pass filter 702 different signals can be directed into the detector 412 and contrast thus procuced. Typically the resolution required in this mode is on the order of 10–500 eV, and the energy window passband is adjustable from 10–500 eV by controlling the size of the aperture/slit 704. The typical energy losses for imaging in this mode will be on the order of 20–5000 eV, which represent the mean inelastic scattering from the thick specimen. The energy pass band is chosen sufficiently wide to differentially enhance contrast by either excluding or selecting inelastic scattering intensity derived from various structural components. The selection/adjustment of the band pass range would be under the control of a computer 420 using a detector control module 430 and/or a lens control module 424 of FIG. 4.

Figure 8:
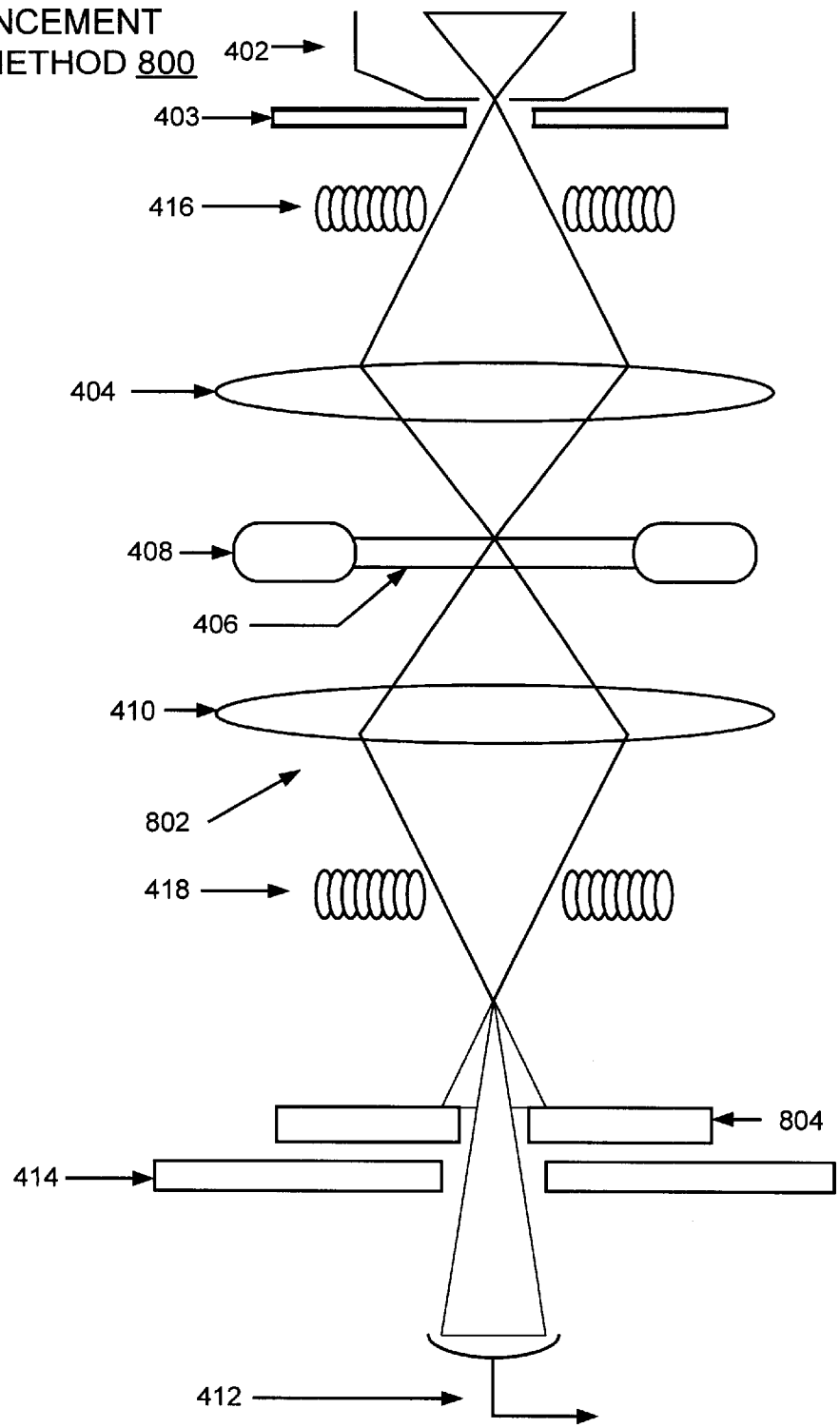
FIG. 8 illustrates a third contrast enhancement method employing an addition of a second annual detector in accordance with the preferred embodiment.

Referring now to FIG. 8, a SCEM configuration generally designated by the reference numeral 800 is shown for a third method for implementing further contrast in the SCEM image. In the SCEM third method configuration 800, the SCEM is then taken just out of confocal imaging mode indicated by reference number 802, as in SCEM first method configuration 600. In SCEM third method configuration 800 an annular detector 804 is provided. As shown, the annular detector 802 is installed above the field limiting or primary detector aperture 414. The signal from the annular detector 804 can be either directly observed or electronically inverted, scaled and mixed with that from the primary detector 412.

Figure 9:
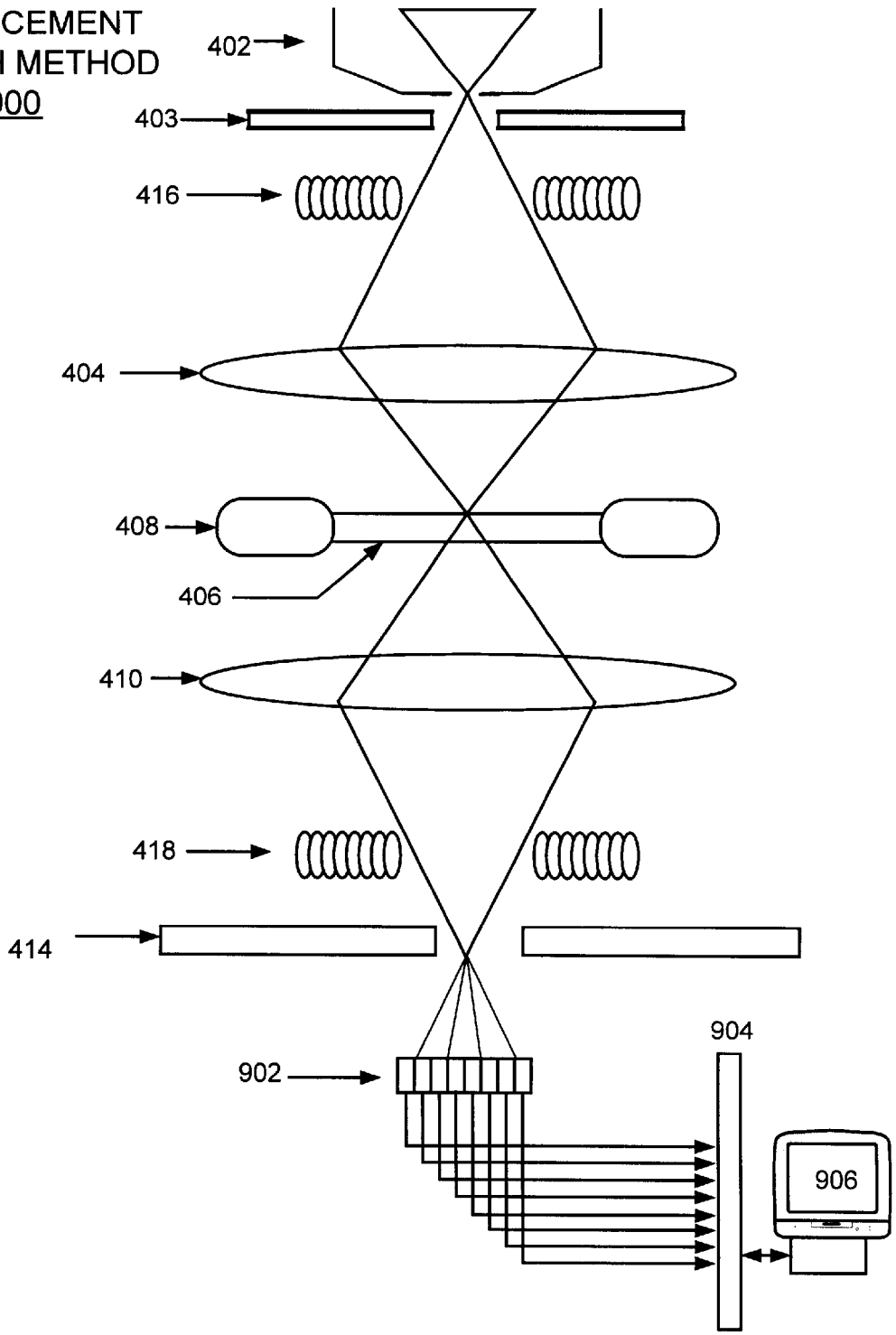
FIG. 9 illustrates a fourth contrast enhancement method employing a charged coupled device (CCD) array in accordance with the preferred embodiment.

Referring now to FIG. 9, a SCEM configuration generally designated by the reference numeral 900 is shown for a fourth method for implementing further contrast in the SCEM image. In the fourth method that is an extension of third method, the two detectors 802 and 804 are replaced by a single two-dimensional detector, such as CCD array (or related two dimensional imaging device) 902 coupled by signal conditioning block 904 to a computer 906 to allow an on-line computer processing of the angularly dispersed signal to be combined in any arbitrary manner as the operator chooses. At the present time this is a CPU intensive processes and is not suitable for near real time imaging, however in the future as computational processing power increases this will become a viable method.

Image resolution in accordance with the present invention is controlled by a number of parameters. Foremost is the initial electron probe size on the entrance surface of the specimen 406. The size of this probe is dictated by the electron gun of illumination source 402 and number of lenses in the pre-specimen optics lens system 404. FIG. 4 illustrates a working implementation of a SCEM 400 that employs only a single pre-specimen lens 404. Configurations have also been implemented using multiple pre-specimen lenses. In general, these configurations increase the resolution by decreasing the attainable probe size. The number of post specimen lenses can be similiarly increased to increase the versatility, however, the effects on resolution is marginal. For thick (>1 $\mu$m) specimens 406 typically used in the SCEM 400, incident probe sizes less than 10 nm are generally not needed.

Figure 10:
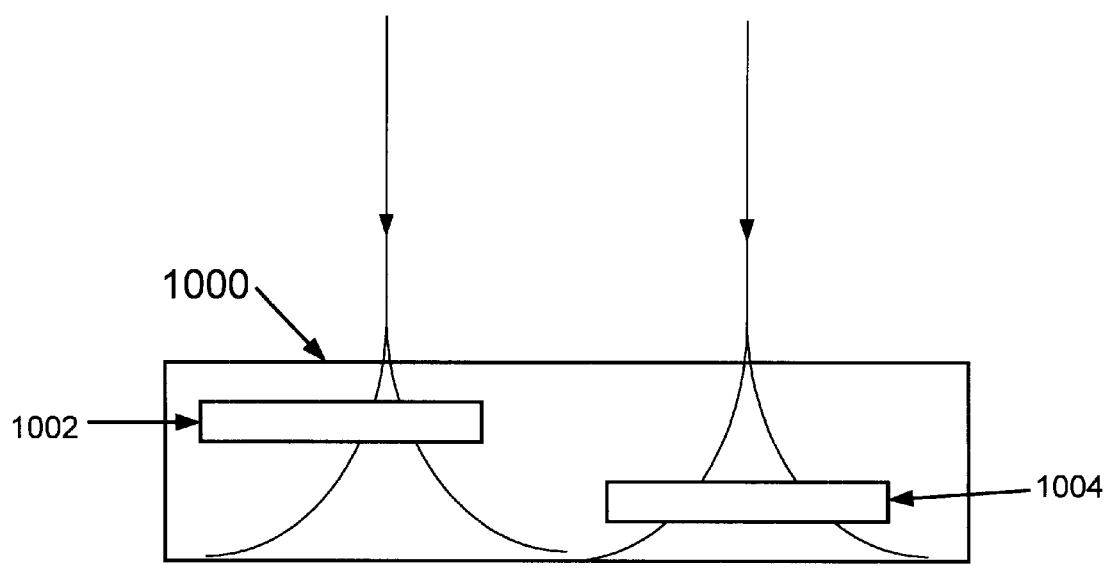
FIG. 10 illustrates a Top And Bottom Effect and the broadening of the illumination probe with thickness in accordance with the preferred embodiment.

Referring now to FIG. 10, there is shown an illustration of a top/bottom effect and the broadening of the illumination probe with thickness of a specimen 1000 in accordance with the preferred embodiment. The resolution in SCEM 400 is directly proportional to the probe diameter which intercepts a feature at each depth in the specimen 1000. Resolution of a first feature 1002 on the left near the top of the specimen will be greater than at a second feature 1004 on the right near the bottom of the specimen 1000. As the illuminating probe propagates through the specimen it gradually increases in diameter due to multiple scattering, this controls the resolution of a feature at a given depth in the specimen. Key to the successful operation of SCEM 400 of the invention is that once the probe has interacted with a specific feature of interest at a specific depth any further scattering by matrix material below it will not decrease the resolution of that feature only broaden the post feature intensity distribution. This means that the resolution of a buried feature is determined by its depth from the entrance surface and the size of the illumination probe at that depth. Features at the entrance surface of the specimen will therefore be imaged at the highest resolution, while those on the bottom surface at the lowest resolution.

Figure 11A:
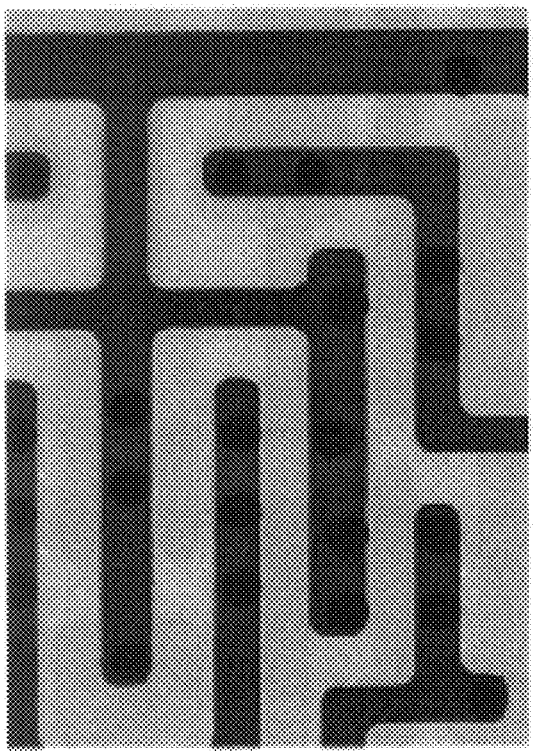
FIGS. 11A and 11B respectively illustrate the Top and Bottom Effect for a ~4 $\mu$m thick specimen in accordance with the preferred embodiment.
Figure 11B:
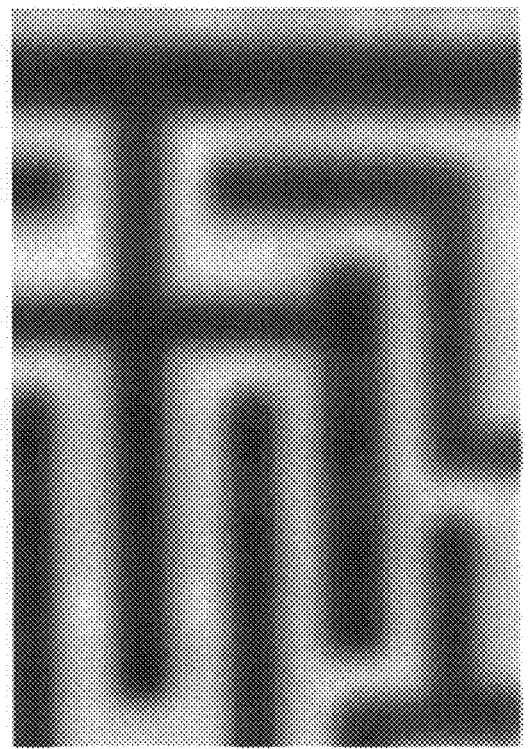

FIGS. 11A and 11B respectively illustrate the top and bottom effect for a ~4 μm thick specimen in accordance with the preferred embodiment. In FIG. 11A, the feature of interest is on the illumination entrance (top) surface and in FIG. 11B the sample is inverted and the same area is now located on the exit (bottom) surface, where the same feature is imaged in a semiconductor sample, at the top surface and at the bottom surface. This is facilitated by simply inverting the specimen in the stage 408. This effect is termed simply the Top/Bottom (T/B) effect. Optimizing conditions to take advantage of the T/B effect is an essential component of this invention. Thus, if a feature of interest is located at a depth beyond the midpoint of the specimen thickness, then image resolution can be improved for any measurement by simply inverting the specimen to exploit the T/B effect.

The image resolution improvement for any measurement at a depth beyond the midpoint of the specimen thickness by simply inverting the specimen to exploit the T/B effect may be understood by reference to FIG. 3, which is a plot of the experimental SCEM image resolution in a semiconductor sample as a function of thickness. In FIG. 3, it can be seen that if an 8 μm thick specimen is studied, and the feature of interest is located at a depth of 7 μm from the entrance surface a nominal resolution of ~150 nm would be achieved. However, if this same specimen is inverted then that same feature of interest would be located only 1 μm in depth from the entrance surface and it would be analyzable at a resolution of ~20 nm. This procedure has been reduced to practice and experimentally verified up to a specimen thickness of ~8 microns in semiconductor specimens.

The resolution of the SCEM 400 is also controlled by the energy of the illumination probe, as such the loss of resolution as a function of depth within the specimen will be a function of this parameter. For the case of electrons, SCEM 400 instruments operating in the 300–400 kV regime are considered optimal due to their reasonable size, their ability to be located within a conventional laboratory sized room and their ability to achieve ~100 nm resolution in specimens of thickness ~8–10 micrometers. Higher voltage SCEM 400 instruments will have greater penetrating power and better resolution for thicker specimens but at a significantly increased cost as well as size. Correspondingly, lower voltage SCEM 400 instruments (200 kV) will be less expensive and smaller but operate at poorer resolution for equivalent thicknesses, or equal resolution but at lesser thicknesses (~100 nm resolution at 3–4 micrometers). The nominal resolution (R) at fixed thickness as a function of accelerating voltage experimentally has been determined to vary according to the relationship $R(t)=R_o \exp(-\alpha(E_o)*t)$. where $R_o$ is the probe diameter at the entrance surface, "t" the depth of the feature of interest, $E_o$ the incident beam energy and $\alpha$, a scattering parameter which varies with $E_o$ and the sample composition.

In brief, the present invention provides a simple technique that can be used to modify existing TEM/STEM systems to a confocal configuration for high image resolution in thick non-transparent specimens. This approach is novel and beautiful in its simplicity. The result, however, is expected to be a powerful new tool for looking at various specimens, such as electronic devices.

While the present invention has been described with reference to the details of the embodiments of the invention shown in the drawing, these details are not intended to limit the scope of the invention as claimed in the appended claims.

What is claimed is:

1. A scanning confocal microscope comprising:
    an illumination source for providing a focused radiation beam, said focused radiation beam not including visible light;
    a specimen, said focused radiation beam applied to said specimen;
    a detector for detecting a interaction signal from said specimen responsive to said applied focused radiation beam; and
    said imaging source, said specimen and said detector being arranged to be located at conjugate image points for configuring the scanning confocal microscope to operate in a confocal imaging mode.

2. A scanning confocal microscope as recited in claim 1 wherein said illumination source for providing a focused radiation beam includes a pre-specimen focusing lens.

3. A scanning confocal microscope as recited in claim 1 wherein said illumination source for providing said focused radiation beam includes an illumination source for providing an electron beam, a proton beam, an ion beam, or an x-ray beam.

4. A scanning confocal microscope as recited in claim 1 wherein said focused radiation beam provided by said illumination source is capable of penetrating thick non-optically transparent specimens.

5. A scanning confocal microscope as recited in claim 4 wherein said thick non-optically transparent specimens have a thickness less than or approximately equal to 10 microns.

6. A scanning confocal microscope as recited in claim 1 wherein said detector for detecting said interaction signal from said specimen responsive to said applied focused radiation beam includes a post-specimen focusing lens.

7. A scanning confocal microscope as recited in claim 1 wherein said detector includes a synchronous de-scanning system for compensating for post-specimen scattering distribution caused by scanning and returning said scattering distribution with said interaction signal from said specimen responsive to said applied focused radiation beam to a conjugate point detector.

8. A scanning confocal microscope as recited in claim 1 wherein said synchronous de-scanning system includes a deflection system of at least one deflection scan coil used with at least one post-specimen focusing lens.

9. A scanning confocal microscope as recited in claim 1 wherein said detector for detecting said interaction signal from said specimen responsive to said applied focused radiation beam includes a post-specimen focusing lens; said post-specimen focusing lens being adjusted from a perfect confocal condition to exclude a portion of high angle scattering of said interaction signal.

10. A scanning confocal microscope as recited in claim 1 wherein said detector for detecting said inter action signal from said specimen responsive to said applied focused radiation beam includes an inelastic energy bandpass filter for differentially enhancing image contrast.

11. A scanning confocal microscope as recited in claim 1 wherein said detector for detecting said interaction signal from said specimen responsive to said applied focused radiation beam includes a field limiting aperture and an annular detector before said field limiting aperture arranged for enhancing image contrast.

12. A scanning confocal microscope as recited in claim 1 wherein detector for detecting said interaction signal from said specimen responsive to said applied focused radiation beam includes a two-dimensional detector for detecting said interaction signal from said specimen responsive to said applied focused radiation beam.

13. A scanning confocal microscope as recited in claim 1 includes a specimen translation stage for controlling 6-axis motion of said specimen including the ability to invert said specimen for exchanging a top illumination surface and a bottom transmission surface; whereby said specimen having a feature located at a depth beyond the midpoint of specimen thickness is inverted for improving image resolution.

14. A scanning confocal microscope as recited in claim 1 wherein said illumination source for providing a focused radiation beam is adapted for providing high image resolution; wherein image resolution is controlled by a combination of an incident probe size, probe current, accelerating voltage, and the depth in the specimen of a feature to be imaged.

15. A scanning confocal microscope as recited in claim 1 includes an interface to a plasma cleaning system for cleaning a specimen stage and specimen.

16. A method for configuring a scanning confocal microscope for imaging of thick non-optically transparent specimens including imaging of structures buried in thick non-optically transparent specimens comprising the steps of:
configuring the scanning confocal microscope to operate in a confocal imaging mode by arranging an illumination source, a specimen and a detector to be located at conjugate image points;
providing a focused radiation beam with said illumination source, said focused radiation beam not including visible light;
applying said focused radiation beam to penetrate the specimen; and
utilizing a detector, detecting an interaction signal from said specimen responsive to said applied focused radiation beam.

17. A method for configuring a scanning confocal microscope for imaging of thick non-optically transparent specimens as recited in claim 16 includes the step of providing said detector with a conjugate point detector and a synchronous de-scanning system for compensating for post-specimen scattering distribution caused by scanning and returning said scattering distribution with said interaction signal from said specimen responsive to said applied focused radiation beam to said conjugate point detector.

18. A method for configuring a scanning confocal microscope for imaging of thick nontransparent specimens as recited in claim 16 includes the step of providing said detector with a post-specimen focusing lens; adjusting said post-specimen focusing lens from a perfect confocal condition to exclude a portion of high angle scattering of said interaction signal or to image different depths in the specimen by utilizing the depth of field adjustment of said post specimen focusing lens.

19. A method for configuring a scanning confocal microscope for imaging of thick non-optically transparent specimens as recited in claim 16 includes the step of providing said detector with an inelastic energy bandpass filter for differentially enhancing image contrast.

20. A method for configuring a scanning confocal microscope for imaging of thick non-optically transparent specimens as recited in claim 16 includes the step of providing said detector with a field limiting aperture and an annular detector before said field limiting aperture arranged for enhancing image contrast.

21. A method for configuring a scanning confocal microscope for imaging of thick non-optically transparent specimens as recited in claim 16 includes the step of providing said detector with a two-dimensional detector for detecting said interaction signal from said specimen responsive to said applied focused radiation beam.

22. A method for configuring a scanning confocal microscope for imaging of thick non-optically transparent specimens as recited in claim 16 includes the step of providing a specimen translation stage for controlling 6-axis motion of said specimen including the ability to invert said specimen for exchanging a top illumination surface and a bottom transmission surface of said specimen; whereby said specimen having a feature located at a depth beyond the midpoint of specimen thickness is inverted for improving image resolution.

23. A method for configuring a scanning confocal microscope for imaging of thick non-optically transparent specimens as recited in claim 16 includes the step of adapting said illumination source for providing high image resolution; wherein image resolution is controlled by a combination of an incident probe size, probe current, accelerating voltage, and the depth in the specimen of a feature to be imaged.

24. A method for configuring a scanning confocal microscope for imaging of thick non-optically transparent specimens as recited in claim 16 includes the step of providing said illumination source for providing an electron beam, a proton beam, an ion beam, or an x-ray beam.

* * * * *